United States Patent
Young et al.

(10) Patent No.: US 6,238,213 B1
(45) Date of Patent: May 29, 2001

(54) SUCTION ORAL BRUSH

(75) Inventors: Charles E. Young; Richard A. Rude, both of Crystal Lake; Paul H. Hanifl, Barrington Hills, all of IL (US)

(73) Assignee: Sage Products, Inc., Crystal Lake, IL (US)

(*) Notice: Subject to any disclaimer, the term of this patent is extended or adjusted under 35 U.S.C. 154(b) by 0 days.

(21) Appl. No.: 09/619,174

(22) Filed: Jul. 19, 2000

(51) Int. Cl.[7] .................................................. A61C 17/06
(52) U.S. Cl. ................................ 433/91; 433/95; 15/322; 132/308
(58) Field of Search .......................... 433/91, 95; 15/322, 15/105; 132/308; 601/162, 164

(56) References Cited

U.S. PATENT DOCUMENTS

| | | | |
|---|---|---|---|
| 1,408,520 | * 3/1922 | Larsen | 401/28 |
| 4,538,631 | * 9/1985 | Prince | 132/308 |
| 5,151,094 | * 9/1992 | Hanifl | 604/902 |
| 5,463,792 | * 11/1995 | Hogan et al. | 15/322 |
| 6,168,434 | * 1/2001 | Bohm-Van Diggelen | 433/141 |

* cited by examiner

Primary Examiner—Gene Mancene
Assistant Examiner—Melba Bumgarner
(74) Attorney, Agent, or Firm—Lee, Mann, Smith, McWilliams, Sweeney & Ohlson

(57) ABSTRACT

A suction oral care device with a head having opposite scrub elements. The scrub elements are dissimilar to one another, one of the scrub elements comprising bristles and the other comprising a foam pad. A suction port communicates with each scrub element, each suction port leading to a suction end of the device. A suction outlet, separate from the suction ports, also extends from the cleansing head. The suction ports and the suction outlet provide three separate locations for suctioning so that even if two become clogged, a third is available.

20 Claims, 1 Drawing Sheet

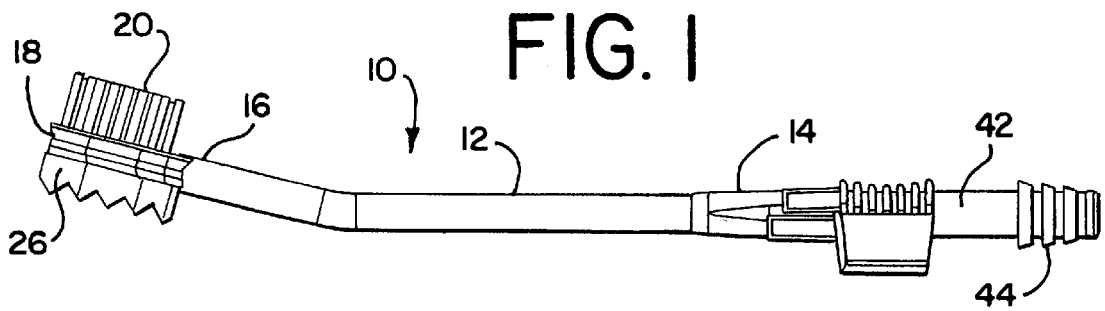
FIG. 1
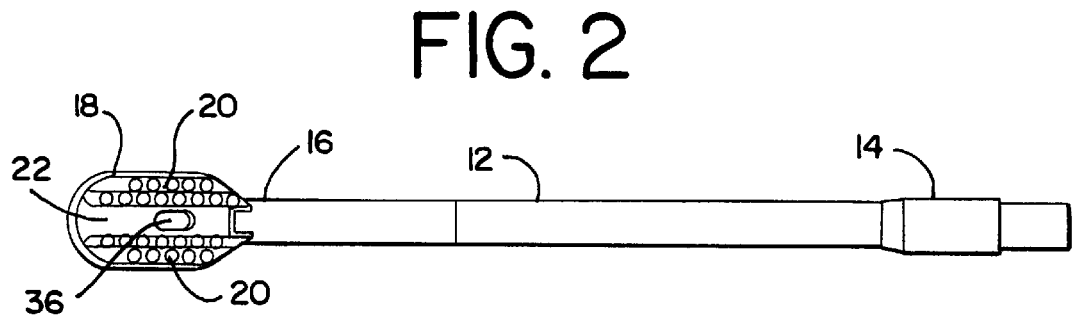
FIG. 2
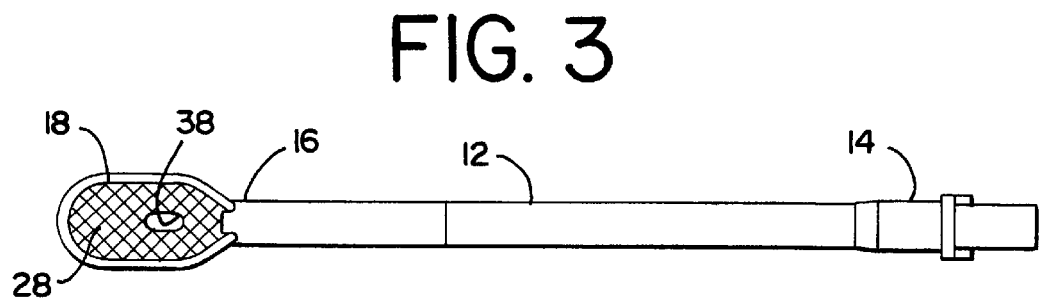
FIG. 3
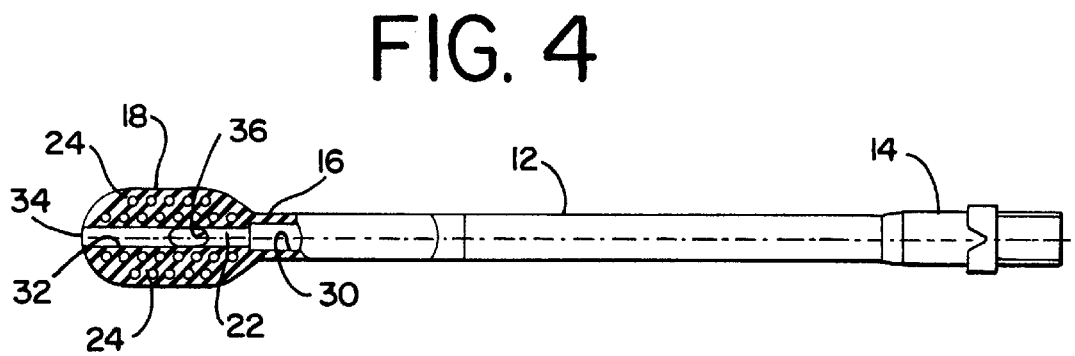
FIG. 4
FIG. 6
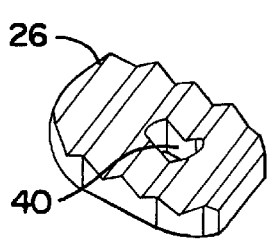
FIG. 5
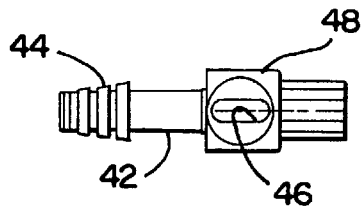

SUCTION ORAL BRUSH

BACKGROUND OF THE INVENTION

This invention relates to oral care devices, and in particular to a suction oral brush configured for eliminating mucus or other liquids, and having a cleaning head with opposite, dissimilar scrub elements.

As explained in U.S. Pat. No. 5,151,094, which is assigned to the assignee of the present invention and the disclosure of which is incorporated herein by reference, oral swabs, normally used for oncology treatments, are well known. Such swabs can be simple swabs which are used and then discarded, or oral suction devices, such as the '094 patent.

While the '094 patent was a substantial improvement over known oral swabs, its utility is somewhat limited. Because its head has only a single type of cleansing element, traditional-type brushing of teeth and gums is not possible. Also, once the suction port becomes clogged during use, the swab must either be cleaned or discarded and replaced. Its use has therefore been somewhat limited by its design.

SUMMARY OF THE INVENTION

The present invention is directed to a suction oral care device of greater utility, while still being disposable. The device has an elongated, hollow shaft having a suction end and a cleansing end. A head is located at the cleansing end, the head having opposite scrub elements. The scrub elements are dissimilar to one another, and a suction port communications with each scrub element. Each suction port leads to the suction end.

In accordance with the preferred form of the invention, a further suction outlet, separate from the suction ports, is also located at the cleansing end. The suction outlet extends from an axial end of the head, between the two suction ports.

A suction control is located at the suction end. The suction control includes a suction regulation opening which is shaped to be manipulated by a thumb or a finger.

One of the scrub elements at the head preferably comprises a series of bristles. A center channel is provided through the bristles, separating the bristles into two clusters. The suction port communicating with the bristles is located in the center channel. Preferably, the center channel is aligned axially in relation to the shaft.

The other of the scrub elements preferably comprises a foam pad. The foam pad includes an orifice aligned with the suction port which communicates with the foam pad to provide a separate source of suction at the foam pad, as well.

BRIEF DESCRIPTION OF THE DRAWING FIGURES

The invention is described in greater detail in the following description of an example embodying the best mode of the invention, taken in conjunction with the drawing figures, in which:

FIG. 1 is a side elevational illustrated of the suction oral care device according to the invention, FIG. 2 is a top plan view of the suction oral care device shown in FIG. 1, slightly enlarged from that shown in FIG. 1, and with the suction connection element omitted, FIG. 3 is a bottom plan view of the suction oral care device of FIG. 1, having the foam pad omitted from the head, and having the suction connection element omitted, FIG. 4, is a view similar to FIG. 2, but with a portion of the head and stem of the device being in cross section to illustrate detail, FIG. 5 is a bottom plan view (in relation to FIG. 1) of the suction connection element of the suction oral care device illustrated in FIG. 1, and FIG. 6 is an enlarged perspective view of the foam pad forming part of the head of the suction oral care device.

DESCRIPTION OF AN EXAMPLE EMBODYING THE BEST MODE OF THE INVENTION

A disposable suction oral care device according to the invention is shown generally at 10 in the drawing figures. The device 10 is composed of an elongated, hollow shaft 12, having a suction end 14 and a cleansing end 16. The shaft 12 can be bent, as illustrated, for greater ease during use, or can be straight.

The cleansing end 16 includes an integral head 18 having opposite flat sides. Scrub elements are located on either of the flat sides. One of the scrub elements comprises a series of bristles 20. The bristles 20 are separated into two clusters as illustrated in FIG. 2, leaving a center channel 22 for passage of liquid and semi-liquid material, as described in further detail below. The bristles 20 can be installed in any conventional fashion, such as forming one side of the head 18 with a series of bristle cavities 24, as shown in FIG. 4, in which the bristles 20 can be inserted. Other means of affixing the bristles 20 in the two clusters will be apparent to one skilled in the art.

The side of the head 18 opposite from that of the bristles 20 carries a resilient scrub element in the form of a foam pad 26. The foam pad 26 adheres to the head 18 in any conventional fashion, and as shown in FIG. 3, the side of the head 18 to which the foam pad 26 adheres can be roughened, with a waffle surface 28, in order to promote good adherence. The foam pad 26 may be ribbed on its working surface or otherwise formed to promote scrubbing and aid in the removal of saliva, mucus and other liquid and semi-liquid material during use of the suction oral care device 10.

The shaft 12 is hollow throughout its length. A portion of the hollow interior, in the form of a central channel 30, is shown in FIG. 4. The central channel 30 is connected to an axially-extending suction channel 32 in the head 18, leading to a suction outlet 34 at the distal end of the head 18. The suction outlet 34 therefore is one source of suction that can be employed when using the suction oral care device 10.

A first suction port 36 extends transversely from the suction channel 32, and is located between the two clusters of bristles 20 in the channel 22. A second suction port 38 extends transversely in the opposite direction from the suction channel 32, and is aligned with an aperture 40 formed in the foam pad 26. The suction ports 36 and 38 therefore form two more suction sources which can be used when the device 10 is employed.

The suction end 14 includes a suction connection 42. The suction connection 42 is provided with a connector 44 which has circumferential ribs shaped to engage a flexible plastic tube or the like (not illustrated) when the suction oral care device 10 is connected to a source of suction. The suction connection 42 is hollow in its interior, and is in communication with the central channel 30 of the shaft 12. The suction connection 42 also includes an opening 46 to its hollow interior, the opening 46 being surrounded by a platform 48 shaped to be engaged by the finger or thumb of a user of the suction oral care device 10. Thus, the user can control the amount of suction experienced at the suction outlet 34 and suction ports 36 and 38 by appropriately covering all or a portion of the opening 46 in a well-known manner.

The suction connection 42 can be an integral extension of the shaft 12, or can be, as illustrated, a separate unit which is fitted on the suction end 14. The means of fitting or connection can be conventional, and are therefore not described in greater detail.

The suction oral care device 10 is used for mouth care, with either the bristles 20 or the foam pad 26 being employed for cleansing. The channel 22 provides for good flow to the suction port 36. Because of the nature of saliva, mucus and other relatively viscous material which might be found in the oral cavity, however, after a period of use, either or both of the suction ports 36 and 38 might become clogged. In that event, however, suction is still available through the suction outlet 34. The suction oral care device 10 is therefore highly versatile, having two scrub elements, the bristles 20 and the foam pad 26, which are dissimilar to one another, and which can be used for various types of mouth care. Even when the suction port 36 between the bristles 20 and the suction port 38 through the foam pad 26 become clogged, the suction oral care device 10 can be used as a suctioning device by appropriately suctioning through the suction channel 32.

One form of the invention has been illustrated in the drawing figures. Various changes can be made to the invention without departing from the spirit thereof or scope of the following claims.

What is claimed is:

1. A suction oral care device, comprising
   a. an elongated, hollow shaft having a suction end and a cleansing end,
   b. a head located at said cleansing end, said head having opposite scrub elements, said scrub elements being dissimilar to one another, and
   c. a suction port communicating with each scrub element, each suction port leading to said suction end.

2. The suction oral care device according to claim 1 including a suction outlet, separate from said suction ports, at said cleansing head and leading to said suction end.

3. The suction oral care device according to claim 2 in which said suction outlet extends from an axial end of said head.

4. The suction oral care device according to claim 1 including a suction control located at said suction end.

5. The suction oral care device according to claim 4 in which said suction control includes a suction regulation opening.

6. The suction oral care device according to claim 5 in which said suction regulation opening is shaped to be manipulated by a thumb or finger.

7. The suction oral care device according to claim 1 in which one of said scrub elements comprises bristles.

8. The suction oral care device according to claim 7 including a center channel through said bristles separating said bristles into two clusters, said port communicating with said bristles being located in said center channel.

9. The suction oral care device according to claim 8 in which said center channel is aligned axially in relation to said shaft.

10. The suction oral care device according to claim 1 in which one of said scrub elements comprises a foam pad.

11. The suction oral care device according to claim 10 in which said foam pad includes an orifice aligned with said port communicating with said foam pad.

12. A suction oral care device, comprising
    a. an elongated, hollow shaft having a suction end and a cleansing end,
    b. a head located at said cleansing end, said head having opposite scrub elements, at least one of said scrub elements comprising bristles,
    c. a suction port communicating with each scrub element, each suction port leading to said suction end, and
    d. a center channel through said bristles separating said bristles into two clusters, said port communicating with said bristles being located in said center channel.

13. The suction oral care device according to claim 12 including a suction outlet, separate from said suction ports, at said cleansing head.

14. The suction oral care device according to claim 13 in which said suction outlet extends from an axial end of said head.

15. The suction oral care device according to claim 12 in which said center channel is aligned axially in relation to said shaft.

16. The suction oral care device according to claim 12 in which one of said scrub elements comprises a foam pad.

17. The suction oral care device according to claim 16 in which said foam pad includes an orifice aligned with said port communicating with said foam pad.

18. The suction oral care device according to claim 12 including a suction control located at said suction end.

19. The suction oral care device according to claim 18 in which said suction control includes a suction regulation opening.

20. The suction oral care device according to claim 19 in which said suction regulation opening is shaped to be manipulated by a thumb or finger.

* * * * *